United States Patent [19]

Bernhardt

[11] 4,301,088

[45] Nov. 17, 1981

[54] METHOD OF PREPARING BENZYL ALCOHOLS BY DECARBONYLATION OF FORMIC ACID ESTERS

[75] Inventor: Günther Bernhardt, St. Augustin, Fed. Rep. of Germany

[73] Assignee: Dynamit Nobel AG, Troisdorf, Fed. Rep. of Germany

[21] Appl. No.: 46,081

[22] Filed: Jun. 6, 1979

[30] Foreign Application Priority Data

Jun. 9, 1978 [DE] Fed. Rep. of Germany ....... 2825362

[51] Int. Cl.$^3$ ...................... C07C 41/18; C07C 29/00
[52] U.S. Cl. .............................. 260/465 F; 568/637; 568/638; 568/648; 568/649; 568/650; 568/764; 568/812
[58] Field of Search ............... 568/764, 814, 811, 715, 568/812, 637, 638, 650, 648, 649; 260/465 F

[56] References Cited

FOREIGN PATENT DOCUMENTS 2603024 11/1977 Fed. Rep. of Germany ...... 568/715

OTHER PUBLICATIONS

Wagner et al., Synthetic Org. Chem. (1953) 169.
Tommila, Chem. Abs., vol. 38, (1944) 6173(3).

*Primary Examiner*—Bernard Helfin
*Attorney, Agent, or Firm*—Sprung, Felfe, Horn, Lynch & Kramer

[57] ABSTRACT

A method for preparing benzyl alcohols or substituted benzyl alcohols is disclosed by decarbonylation of formic acid esters of benzyl alcohols or ring substituted benzyl alcohols, the decarbonylation being carried out in the presence of a catalyst.

32 Claims, No Drawings

METHOD OF PREPARING BENZYL ALCOHOLS BY DECARBONYLATION OF FORMIC ACID ESTERS

BACKGROUND OF THE INVENTION

1. Field of the Invention

This invention relates to a method of preparation of benzyl alcohols or ring substituted benzyl alcohols by decarbonylation of formic acid esters of benzyl alcohol or ring substituted benzyl alcohols. More especially, this invention relates to such a decarbonylation carried out in the presence of a catalyst to provide benzyl alcohols or ring substituted benzyl alcohols with a high volume/time yield.

2. Discussion of the Prior Art

Benzyl alcohols are valuable starting compounds for the preparation of aromatic aldehydes.

Hydroxymethylbenzyl alcohols (xylylene glycols) are valuable intermediates in organic syntheses and also are used in the preparation of polyesters and polyurethanes.

It is known that ethyl formiate is cleaved in the presence of sodium alcoholate to ethanol and carbon monoxide (Chem. Zentralblatt 39 [1868] 632; Journ. Amer. Chem. Soc. 50 [1928] 235; Berichte 65 [1932] 954). It is disadvantageous, however, that the transformation is poor and large amounts of sodium alcoholate are required for the cleavage.

Other strong bases, such as sodium hydride, potassium tert.-butylate and triphenyl methyl sodium have been used for the decarbonylation of ethyl formiate and butyl formiate (Journ. Org. Chem. 31 [1966] 2623). By this method high transformations of the formic acid esters are achieved, but it is difficult to perform, and it is also uneconomical. For example, stoichiometric amounts of the very expensive bases are required. In the decarbonylation, the reaction products are first the metal salts of the alcohols, and the alcohols have to be released from them by hydrolysis and isolated by extraction from aqueous solution.

It is also known to cleave phenyl formiate, in the presence of stoichiometric amounts of sodium amide, to sodium phenolate, carbon monoxide and ammonia. This method also has the disadvantage that it is technically complicated and uneconomical, since large amounts of sodium amide must be used, and the phenol has to be released from its sodium salt (Comptes Rendus 178 [1924] 1583).

Methods have also become known for the decarbonylation for formic acid esters of aliphatic alcohols by the use of hydrogenation catalysts to form alcohols. For example, in German Pat. No. 1,805,403, there is described a method for the decarbonylation of formic acid esters of aliphatic alcohols having a carbon number of 1 to 9 on copper-nickel mixed catalysts; it is, however, a decided disadvantage that the decarbonylation is not selective and, in addition to the alcohols, the corresponding aldehydes form as accompanying products, and are very difficult to separate from the alcohols.

On the other hand, it is known that n-octyl formiate can be cleaved to octanol and carbon monoxide with a high yield in the presence of palladium-carbon catalysts (Journ. Org. Chem. 35 [1970] 1694). This method of decarbonylation, however, fails completely in the case of the araliphatic formic acid ester benzyl formiate, which is cleaved in a virtually quantitative manner to toluene and carbon dioxide on the same catalyst.

SUMMARY OF THE INVENTION

It is the object of the present invention to make available an economical method, which can be practiced in a simple manner on a commercial scale, and which will permit the preparation of benzyl alcohols with a high volume/time yield.

This object is achieved, in accordance with the invention, by decarbonylating the formic acid esters of the benzyl alcohols or of the substituted-ring benzyl alcohols in the presence of a catalyst.

In this reaction of the benzyl formiate, which is different from the reaction of formic acid esters of aliphatic alcohols, it is surprising, in view of the necessity of using stoichiometric amounts of a base for the quantitative decarbonylation of formic acid esters of aliphatic alcohols and phenols, that the cleavage of formic acid esters of benzyl alcohols and substituted-ring benzyl alcohols to the corresponding alcohols and carbon monoxide in the presence of even very small amounts of a strong base, takes place within a very short time and with a high transformation. Generally, the process of the invention is carried out using 0.01 to 15 mol percent, preferably 0.05 to 8 mol percent, based upon the mols for formic acid ester to be decarbonylated.

Benzyl alcohol formic acid esters which can be decarbonylated by the method of the invention, and which are substituted one or more times in the benzene ring, include those which can be described by the following general formula:

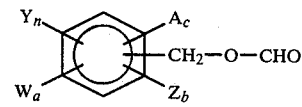

in which the substituents
  Y=halogen, especially Cl or Br, and/or alkyl groups (n=0 to 5, preferably 0 to 2),
  W=—CH$_2$—O—CHO (a=0 to 5, preferably 0 to 2), and
  Z=OH— and/or alkoxy, preferably methoxy, and/or phenoxy groups (b=0 to 3, preferably 0 to 2), and
  A=nitrile groups (c=0 to 2),
  a+b+n+c=1 to 5, preferably 1 to 3.

The alkyl groups or alkoxy groups are those having from one to eight carbon atoms, preferably those having one to four carbon atoms, straight-chained or branched, especially methyl groups and methoxy groups. The phenoxy groups can have substituents, e.g., Cl or Br, or the above-named substituents, such as alkyl groups, for example. The substituents of the benzene ring of the phenoxy groups can be the same as or different from the substituents of the benzene ring shown in the formula.

Preferentially used formic acid esters are benzyl formiate or mono- or di-substituted benzyl formiates, the substituents being able to be the same or different, and are halogen, alkyl groups, alkoxy groups, phenoxy groups or formoxymethyl groups.

The following are given as examples of substituted-ring benzyl formiates having a formoxymethyl substituent in the ortho, meta or para position: xylylene glycol bisformiates, those having in addition to the formoxymethyl substituent one or more additional substituents in the benzene ring, e.g., chlorine or bromine substituents, such as, for example, monochloro- and dichloroxylylene glycol bisformiates, monoalkyl-substituted xylylene glycol bisformiates, or dialkyl-substituted xylylene glycol bisformiates, such as, for example, mono- or di-$C_1$ to $C_4$-alkyl-substituted xylylene glycol bisformiates, such as, for example, dimethyl- or diethylxylylene glycol bisformiates, alkoxy-substituted xylylene glycol bisformiates, such as dimethoxyxylylene glycol bisformiates and the corresponding hydroxy-substituted xylylene glycol bisformiates such as mono- and di-hydroxybisformiates.

Other substituted-ring formiates which can be decarbonylated by the method of the invention are, for example, benzyl monoformiates having chlorine or bromine substituents and/or alkyl groups, such as methyl groups and/or alkoxy groups such as methoxy and/or cyano groups, in the ortho and/or meta and/or para position with respect to the formoxymethyl group.

The following are given as examples: o- or m- or p-methylbenzyl formiate, o- or m- or p-phenoxybenzyl formiate, o- or m- or p-chlorobenzyl formiate, o- or m- or p-bromobenzyl formiate, dimethylbenzyl formiates, o- or m- or p-hydroxybenzyl formiate, o- or m- or p-methoxybenzyl formiate, dichloro- or trichloro- or di-bromo- or tribromobenzyl formiate, tetrachlorobenzyl formiate, tetrabromobenzyl formiate, pentabromobenzyl formiate, and o- or m- or p-cyanobenzyl formiate.

Particular starting compounds are benzyl formiate, and benzyl formiates which are substituted in the ortho, meta or para position, such as, for example, chloro-, dichloro-, bromo-, methyl-, dimethyl-, methoxy-, phenoxy-, hydroxy- and formoxy-methyl benzyl formiate.

Strongly basic decarbonylation catalysts are the alcoholates, especially $C_1$-$C_8$ alkanolates, hydrides, amides and organometallic compounds of the elements of Groups I to III, especially I and II, of the Periodic Table of the Elements. The metallic catalysts are elements of Group I.

The strongly basic decarbonylation catalysts can be described by the following general formula:

$$Me\ R_m \qquad\qquad II$$

in which
Me is a metal of Groups I to III of the Periodic Table of the Elements,
m = 1 to 3, and
R represents the following:
(a) —$OR^1$, $R^1$ being a linear or branched alkyl moiety having 1 to 8, preferably 1 to 4, carbon atoms, or an aryl moiety, e.g., phenyl, or an aralkyl moiety, e.g., phenyl $C_{1-8}$ alkyl, or
(b) an alkyl moiety having 1 to 8, preferably 1 to 4, carbon atoms, or an aryl, e.g., phenyl, or an aralkyl moiety, e.g., phenyl $C_{1-8}$ alkyl, or an amino group, or hydrogen, or
(c) —$OR^2OH$, $R^2$ being a linear or branched alkylene moiety having 2 to 8, preferably 2 to 4, carbon atoms, or an o-, m- or p-xylylene moiety or an o-, m- or p-phenylene moiety or a naphthylene moiety, or,
(d) when Me is an alkali metal, —$OR^2OMe$, $R^2$ being a linear or branched alkylene moiety having 2 to 8, preferably 2 to 4, carbon atoms, or an o-, m- or p-xylylene moiety or an o- or m- or p-phenylene moiety, or a naphthylene moiety.

Preferred metal components of the alcoholates, hydrides and amides, and organometallic compounds are: sodium, potassium, lithium, magnesium and calcium. Preferred metallic catalysts are sodium and potassium.

In the case of the alcoholates, the alcohol component is a monovalent or bivalent primary, a secondary or a tertiary aliphatic, cycloaliphatic or aralaphatic alcohol. Preferably it consists of a $C_1$ to $C_8$ alcohol, such as methanol, ethanol, n-propanol, isopropanol, n-, iso-, sec- or tert.-butanol, cyclohexanol, benzyl alcohol and xylylene glycol. In the case of bivalent alcohols it is preferred to use the alkali alcoholates which have one more free OH group. Alkali phenolates can also be used.

The organic moieties in organometallic compounds are the $C_1$- to $C_{10}$-alkyl or -aryl moieties, such as methyl, ethyl, propyl, isopropyl, n-, iso-, sec- and tert-butyl, octyl, phenyl and naphthyl.

In organometallic compounds of the Grignard type, a halogen atom such as chlorine, bromine or iodine can be present in addition to the alkyl moiety or cycloalkyl or aryl moiety or aralkyl moiety.

The alkali alcoholates are used preferentially as decarbonylation catalysts.

The decarbonylation catalysts are used in amounts of about 0.01 to 10 weight-parts, preferably 0.05 to 5 weight-parts, for each 100 weight-parts of the benzyl formiate.

The catalyst can be used in solid, dissolved or suspended form.

Suitable solvents for alcoholates are, for example, the corresponding alcohols. Suspension agents for hydrides, amides and alkali metals are high-boiling hydrocarbons, such as for example benzine, toluene or xylene.

$C_4$ to $C_7$ hydrocarbons are suitable as solvents for organometallic compounds. Solvents for Grignard compounds are ethers, such as diethyl ether, dibutyl ether and anisole.

The method of the invention is practiced under such conditions that the formic acid ester put in, and advantageously also the resulting alcohol, are in fluid form. For the performance of the process of the invention, for example, the formic acid ester, mixed with the catalyst, can be heated to at least such temperatures that the ester, and also the resultant alcohol if desired, are in the molten state. It is desirable to keep the reaction mixture in movement during the decarbonylation, and to remove the carbon monoxide as it forms.

In general, the temperatures are to be between 20° and 250° C., preferably between 30° and 220° C., depending on the components put in. The optimum temperatures should be determined by preliminary experiment.

The decarbonylation can also be performed in the presence of inert solvents as the reaction medium. The inert solvents are preferably those having boiling points at or above the decarbonylation temperature that is required. Suitable inert solvents, for example, are the alcohols on which the formic acid esters are based, or tertiary alcohols such as tert.-butanol. It is preferred to use the alcohols corresponding to the formic acid esters.

The decarbonylation is performed preferably under standard pressure conditions, although operation at elevated or reduced pressure is not to be excluded. Generally, a pressure from 0.1 Torr to 1.5 atmospheres can be employed, with atmospheric pressure being preferred.

In a preferred embodiment of the method of the invention, the alcohol on which the formic acid ester is based is mixed with the catalyst and placed in the reactor to serve as the reaction medium. The mixture is heated to the decarbonylation temperature of the ester, and, with the continued input of energy, the formic acid ester is fed from a heated tank to the reactor in fluid form at such a rate that a rapid, continuous stream of carbon monoxide is developed. By this procedure, the excessive foaming of the reactor content is prevented.

Alternatively, one can decarbonylate a small portion of the formic acid ester of the alcohol in the presence of the catalyst, and then feed in the remainder of the ester in the manner described.

The reaction medium to be used is to amount preferably to not more than 50 percent of the weight of the formic acid ester that is to be decarbonylated.

Advantageously, when the reaction is completed, all but a portion of the reaction material is removed from the reactor, and the portion that remains is then used as the reaction medium for the next decarbonylation.

The carbon monoxide escaping from the reactor can be flared off through a scrubber and a safety vessel consisting, for example, of a submerged pot or siphon, or it can be collected in a gasometer. The carbon monoxide has a purity of better than 99.9 percent, and it can be reused in chemical reactions, such as carbonylations, for example.

The substance remaining in the reactor consists of a high-percentage benzyl alcohol, and a simple vacuum distillation is performed or, if it is solid, a recrystallization is performed for the purpose of recovering it in pure form.

Yields of the pure benzyl alcohol of as much as 99 percent can be achieved by the method of the invention.

By the the method of the invention, very valuable alcohols can be obtained in a high yield in a simple and ecologically sound manner.

High-purity carbon monoxide is formed as a reusable by-product.

Since only small amounts of adjuvants are required for the decarbonylation and the reaction time is short, a high volume/time yield is achieved in the decarbonylation described in accordance with the invention.

Since no reaction products requiring condensation are formed and no pressure has to be applied during the reaction, very simple reactors suffice.

The formic acid esters of the unsubstituted or substituted-ring benzyl alcohols used as starting products can be prepared by the methods described, for example, in U.S. application Ser. No. 974,468, filed Dec. 29, 1978, assigned to the assignee hereof, the disclosure of which is hereby incorporated herein by reference. In these methods, benzyl chloride and/or benzyl bromide or mono- or polysubstituted-ring benzyl chlorides and/or benzyl bromides or xylylene dichlorides and/or xylylene dibromides, as well as their substituted-ring derivatives are reacted with an alkali or alkaline earth formiate with heating, in the presence of a catalyst, to the corresponding benzyl formiates or xylylene glycol bisformiates. The reaction is performed preferably in the heterogeneous phase, without the use of a solvent, at a temperature at which the halide used is in the molten phase and the alkali or alkaline earth formiate is in the solid phase. The reaction is performed generally at temperatures between 100° and 250° C., preferably between 110° and 200° C. Depending on the reaction components, however, the temperatures can also be above or below the stated range. The alkali and alkaline earth formiates are used at least in the amount stoichiometrically required for the completion of the reaction, which is one equivalent for each equivalent of benzyl halide. It is preferable to use excess amounts of formiate. The ratio of equivalents of benzyl halide to alkali formiate or alkaline earth formiate amounts generally to from 1:1 to 1:1.5, preferably from 1:more than 1 to 1:1.1.

Suitable catalysts are tertiary amines, tertiary phosphines, quaternary ammonium salts and quaternary phosphonium salts.

Suitable tertiary amines are, for example, triethylamine, tripropylamine, tributylamine, dimethylaniline, N-methyl morpholine, hexamethylene tetramine, triethylene diamine, and the like, preferably triethylamine. Examples of the tertiary phosphines are triethylphosphine, tributylphosphine, triphenylphosphine, and tribenzylphosphine, preferably triphenylphosphine.

Examples of suitable quaternary ammonium salts are methyltricaprylylammonium chloride, trimethylbenzylammonium chloride, triethylbenzylammonium chloride, and tetrabutylammonium chloride, trimethyl- or triethylbenzylammonium chloride being preferred.

Suitable quaternary phosphonium salts are, for example, triphenylmethyl- or triphenylethylphosphonium bromide.

The catalysts are used, as a rule, in amounts of 0.1 to 10 parts, preferably 0.5 to 5 parts, by weight, for each 100 parts by weight of benzyl halide.

The reaction is performed preferably at standard pressure, although elevated pressure, in an autoclave for example, can be used.

EXAMPLES

EXAMPLE 1

In a four-necked flask provided with stirrer, thermometer, heated dropping funnel and gas exhaust tube, 19.4 g (0.1 mole) of p-xylyleneglycol bisformiate and 6 g (0.04 mole) of monosodium p-xylene glycolate were combined, the gas exhaust tube was connected to a gas collecting vessel using water as the sealing liquid, and the mixture was heated in the flask at 90° C.

After the bisformiate had completely melted and pressure equilibrium had been established in the gas collecting vessel, the stirrer was turned on and the contents of the flask were heated at 150° C. A vigorous development of carbon monoxide began at 110° C.

After the initial turbulent reaction had abated, 174.6 grams (0.9 mole) of molten p-xylylene glycol bisformiate was fed through the dropping funnel, heated at 100° C., at such a rate that a lively, continuous stream of carbon monoxide gas developed, the flask heater continuing to operate so as to keep the reaction in progress, and the temperature in the flask did not drop below 120° C. The reaction ended after three quarters of an hour.

The amount of carbon monoxide gas that escaped was 43.5 liters (1.94 moles). The material remaining in the reaction flask was vacuum-distilled. At a pressure of 0.5 Torr and a temperature of 140° to 142° C., 131.4 g of p-xylylene glycol distilled over, corresponding to a yield of 95.2% of the theory. The melting point was 116°–117° C.

EXAMPLE 2

In the manner described in Example 1, 19.4 g (0.1 mole) of m-xylylene glycol bisformiate was heated with 5.5 g (0.035 mole) of monosodium m-xylylene glycolate at 130° C., and after the initially vigorous reaction had abated, an additional 174.6 g (0.9 mole) of m-xylylene glycol bisformiate was added drop by drop over a period of 40 minutes. The amount of carbon monoxide formed amounted to 42.6 liters (1.9 moles). After distillation of the material remaining in the flask at 0.2 Torr and 124° to 126° C., 132.5 grams (=96%) of m-xylylene glycol was obtained, having a melting point of 55°–56° C.

EXAMPLE 3

In a four-necked flask equipped as in Example 1, 20 g of p-xylylene glycol containing 6.5 g of monosodium p-xylylene glycolate was heated at 130° C. and 194 g of p-xylylene glycol bisformiate was fed into it, with continued stirring and heating, at such a rate that all of it had been added by the end of 30 minutes. 35 minutes later the evolution of gas had ended. The amount of carbon monoxide that was formed amounted to 43.7 liters (1.95 moles). After distillation of the amount left in the reaction flask had been distilled, 133.2 g of distillate was obtained, having a melting point of 115.5°–116.5° C. This corresponds to a xylylene glycol yield of 96.5% of the theory, after subtracting the xylylene glycol used at the start-up.

EXAMPLES 4a to 4g

In each of these examples, 194 g of p-xylylene glycol bisformiate was reacted in the manner described in Example 1, in the presence of the catalysts listed in Table 1.

The yields given in Table 1 can be further increased if, after the reaction, an amount of water equivalent to the catalyst is added to the residue remaining in the flask, the alkali or alkaline earth base released by hydrolysis is neutralized by the introduction of carbon dioxide, and then the vacuum distillation is performed.

gas meter, the carbon monoxide was passed through a safety pot filled with water, and then was flared off.

The autoclave heating was continued and 7.2 kg of molten p-xylylene glycol bisformiate was fed into the autoclave through the dropping funnel over a period of two hours at such a rate that a continuous, strong current of carbon monoxide escaped. The temperature of the autoclave content fluctuated between 120° and 130° C.

When the formation of gas had ended, 1845.2 liters of gas had been formed (82.3 moles).

All but one-tenth of the contents of the autoclave was removed through the bottom drain valve at 130° C. 222 grams of monosodium p-xylylene glycolate were added, and once again 6 kilograms of p-xylylene glycol bisformiate were fed into the mixture with stirring, at 135° C., as described before, whereupon 1384.5 liters of carbon monoxide gas were released.

The procedure of partially emptying the autoclave, replacing the catalyst let out with the material, and the feeding in of 6 kg of p-xylylene glycol bisformiate was then repeated two more times, and then the autoclave was completely emptied.

The total amount of carbon monoxide released amounted to 5998.7 liters (267.8 moles).

The combined reaction products, which solidified when cold, had a melting point of 113°–114° C.

After distillation at 0.5 Torr and 140°–142° C., 17.6 kg of p-xylylene glycol was obtained, corresponding to a yield of 95% of the theory. The distillate had a melting point of 115.5°–116.5° C.

EXAMPLE 6

In a four-necked flask equipped as in Example 1, 20 g of o-methylbenzyl formiate and 1.8 g of sodium methylate were heated at 110° C., and after the initial vigorous evolution of carbon monoxide had abated, another

TABLE 1

| Example No. | Catalyst [name] | [g] | [moles] | Solvent or suspending agent [ml] | Reaction Time [minutes] | Carbon monoxide [l] | [moles] | p-Xylylene glycol [g] | [% of theory] | Melting Point [°C.] |
|---|---|---|---|---|---|---|---|---|---|---|
| 4(a) | Potassium tert.-butylate | 4.4 | 0.04 | | 40 | 44.6 | 1.99 | 130.0 | 94.2 | 115–116 |
| 4(b) | Sodium amide | 2.5 | 0.06 | — | 50 | 43.2 | 1.93 | 129.9 | 94.0 | 115–116 |
| 4(c) | Sodium methylate | 2.5 | 0.05 | Methanol (15) | 45 | 43.5 | 1.94 | 130.5 | 94.6 | 115.5–116.5 |
| 4(d) | Sodium | 1.0 | 0.04 | Xylene (10) | 60 | 43.0 | 1.92 | 124.2 | 90.0 | 115–116 |
| 4(e) | Butyl lithium | 2.5 | 0.04 | Hexane (15) | 50 | 44.4 | 1.98 | 131.2 | 94.9 | 115–116 |
| 4(f) | Phenyl-magnesium bromide | 7.2 | 0.04 | Anisole (10) | 53 | 43.2 | 1.93 | 130.6 | 94.6 | 115–116 |
| 4(g) | Calcium hydride | 1.8 | 0.04 | — | 71 | 42.6 | 1.90 | 126.4 | 91.6 | 116–117 |

EXAMPLE 5

In a sixteen-liter Pfaudler autoclave equipped with an impeller, a bottom drain valve, a heated dropping funnel, a gas exhaust tube and a sealed gas meter, a mixture of 0.8 kg of p-xylylene glycol bisformiate and 247 g of monosodium p-xylylene glycolate was heated to just above the melting point of the p-xylylene glycol bisformiate (M.P. 84° C.), and, when the melting was complete, the stirrer was started up at 355 rpm. The autoclave was heated up with steam of a temperature of 150° C., and, at a mass temperature of 110° C., the evolution of carbon monoxide began. After passing through the 112.4 g of o-methylbenzyl formiate was fed in, the temperature of the reaction mass being held between 110° and 130° C.

The total amount of carbon monoxide liberated was 18.7 liters (0.95 moles).

After the distillation of the amount remaining in the flask at 10 Torr and 105° to 107° C., 100.2 g of o-methylbenzyl alcohol having a melting point of 36° C. was obtained, which amounts to a yield of 93%.

EXAMPLES 7a to 7i

The benzyl formiates listed in Table 2 were decarbonylated in the presence of sodium methylate as in Example 6. The molar ratio of benzyl formiate to sodium methylate was 1:0.037.

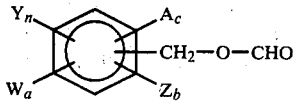

I

TABLE 2

| Example | Formiates [chemical names] | [g] | [moles] | Reaction time [min] | Carbon monoxide [moles] | Alcohol [g & % of theory] | Melting Point [°C.] | Boiling Point [°C.] |
|---|---|---|---|---|---|---|---|---|
| 7a | Benzyl formiate | 136 | 1 | 45 | 0.96 | Benzyl alcohol (103.8/96.1) | — | 93 (10 mm) |
| 7b | m-Methylbenzyl formiate | 140.5 | 0.94 | 42 | 0.94 | m-Methylbenzyl alcohol (108.6/94.7) | <20 | 104–105 (12 mm) |
| 7c | o-Chlorobenzyl formiate | 158.5 | 0.93 | 45 | 0.93 | o-Chlorobenzyl alcohol (129.1/97.0) | 70 | 113.5–114.5 (12 mm) |
| 7d | o-Methoxybenzyl formiate | 83 | 0.5 | 30 | 0.49 | o-Methoxybenzyl alcohol (65.6/95.0) | <20 | 131–132 (15 mm) |
| 7e | 2,4-Dimethylbenzyl formiate | 164 | 1 | 45 | 0.95 | 2,4-Dimethylbenzyl alcohol (129.6/95.3) | 28–29 | 120 (12 mm) |
| 7f | m-Phenoxybenzyl formiate | 228 | 1 | 30 | 0.99 | m-Phenoxybenzyl alcohol (190.0/95.0) | <20 | 142–144 (0.6 mm) |
| 7g | p-Hydroxybenzyl formiate | 132.2 | 0.87 | 33 | 0.86 | p-Hydroxybenzyl alcohol (102.5/95.0) | 124 | — |
| 7h | p-Cyanobenzyl formiate | 161 | 1.0 | 45 | 0.95 | p-cyanobenzyl alcohol (126.1/94.8) | 134–135 | — |
| 7i | 2,5-dichloro-p-xylylene glycol bis-formiate | 131.5 | 0.5 | 44 | 0.43 | 2,5-Dichloro-p-xylylene glycol (96.3/93.0) | 201–202 | |

EXAMPLE 8

In a four-necked flask equipped as in Example 1, 10.4 grams of o-xylylene glycol bisformiate (0.05 mole) and 1.8 kilograms of sodium methylate were heated at 120° C. and, after the initial vigorous evolution of carbon monoxide had abated, another 93.4 grams of o-xylylene glycol bisformiate (0.48 mole) were fed in at 120° C. over a period of 45 minutes. The total amount of carbon monoxide liberated was 23.4 liters (1.04 moles).

After distillation of the residue remaining in the flask at 0.2 Torr and 122°–124° C., 68.5 grams, amounting to 92.8% of the theory, of o-xylylene glycol was obtained having a melting point of 63.5°–64.5° C.

What is claimed is:

1. A method for preparing a benzyl alcohol or ring-substituted benzyl alcohol which comprises decarbonylating a formic acid ester of the corresponding benzyl alcohol in the presence of 0.01 to 15 mol percent of a strong base as catalyst by heating at a temperature sufficient to effect carbon monoxide evolution said formic acid ester in the presence of said strong base in a reaction mixture consisting essentially of said formic acid ester and said catalyst, the process being carried out either in the melt or in the presence of a solvent, the solvent being a tertiary alcohol or an alcohol corresponding to the formic acid ester reactant, the decarbonylation being carried out at a temperature at which the formic acid ester employed and the resulting alcohol are in fluid form.

2. A method according to claim 1 wherein the formic acid ester to be decarbonylated is a formic acid ester of the general formula which are mono- or polysubstituted on the benzene ring and in which the substituents are as follows:
Y is halogen or alkyl and n is 0 to 5;
W is —CH$_2$—O—CHO and a is 0 to 5;
Z is hydroxy and/or alkoxy and/or phenoxy and b is 0 to 3;
A is a nitrile and c is 0 to 2; and
a+b+n+c=1 to 5.

3. A method according to claim 2 wherein a+b+n+c=1 to 3.

4. A method according to claim 2 wherein Y is chloro or bromo or a C$_1$–C$_8$ alkyl group and n is 0 to 2.

5. A method according to claim 2 wherein W is —CH$_2$—O—CHO and a is 0 to 2.

6. A method according to claim 2 wherein Z is hydroxy or methoxy or phenoxy and b is 0 to 2.

7. A method according to claim 2 wherein A is a nitrile group and c is 0 to 2.

8. A method according to claim 1 wherein the formic acid ester is a mono- or disubstituted benzyl formiate, the substituents on the phenyl ring being of the group consisting of halogen, alkyl, alkoxy, phenoxy or formoxymethyl, the substituents being the same or different from one another when the phenyl ring is disubstituted.

9. A method according to claim 1 wherein the catalyst has the formula

Me R$_m$   II wherein
Me represents a metal of Group I to Group III of the Periodic System, m represents 1 to 3, and
R has any of the following meanings:
(a) —OR$^1$ where R$^1$ represents a linear or branched alkyl moiety having 1 to 8 carbon atoms or an aryl moiety or an aralkyl moiety;
(b) an alkyl moiety having 1 to 8 carbon atoms or an aryl moiety or an aralkyl moiety or an amino group or hydrogen;
(c) —OR$^2$OH where R$^2$ is a linear or branched alkylene moiety having 2 to 8 carbon atoms or an o-, m- or p-xylylene moiety or an o-, m- or p-phenylene moiety or a naphthylene moiety;
(d) where Me is an alkali metal, R is —OR$^2$OMe where R$^2$ is a linear or branched alkylene moiety having 2 to 8 carbon atoms or an o-, m- or p-xylylene moiety or an o-, m- or p-phenylene moiety or a naphthylene moiety.

10. A method according to claim 9 wherein R has the meaning —OR$^1$ where R$^1$ is a linear or branched alkylene moiety having 1 to 4 carbon atoms or phenyl or a phenyl C$_1$–C$_8$ alkyl moiety.

11. A method according to claim 9 wherein R is an alkyl moiety of 1 to 4 carbon atoms, phenyl, a phenyl C$_1$–C$_8$ alkyl moiety, an amino group or hydrogen.

12. A method according to claim 9 wherein R has the meaning —OR$^2$OH where R$^2$ is a linear or branched alkylene moiety of 2 to 4 carbon atoms, an o-, m- or p-xylylene moiety, an o-, m- or p-phenylene moiety or a naphthylene moiety.

13. A method according to claim 9 wherein Me is an alkali metal and R has the meaning —OR$^2$OMe where R$^2$ is a linear or branched alkylene moiety of 2 to 4 carbon atoms, an o-, m- or p-xylylene moiety, an o-, m- or p-phenylene moiety or a naphthylene moiety.

14. A method according to claim 9 wherein the decarbonylation catalyst is a lithium-, sodium-, potassium-, magnesium- or calcium-methylate, -ethylate, -tertiary butylate, -benzylate, -xylene glycolate or -phenolate.

15. A process according to claim 9 wherein the decarbonylation catalyst is a lithium-, sodium-, potassium-, calcium-, or aluminim-hydride.

16. A process according to claim 9 wherein the decarbonylation catalyst is a lithium-, sodium- or potassium-butyl, -phenyl or -naphthyl.

17. A process according to claim 1 wherein the decarbonylation catalyst is a Grignard compound.

18. A process according to claim 1 wherein the decarbonylation catalyst is an alkali metal.

19. A process according to claim 18 wherein said alkali metal is sodium or potassium.

20. A process according to claim 1 wherein the decarbonylation catalyst is present in an amount of 0.01 to 10 weight percent, based upon the amount of formiate to be decarbonylated.

21. A process according to claim 20 wherein said decarbonylation catalyst is present in an amount of 0.05 to 5 weight percent, with respect to the formiate to be decarbonylated.

22. A process according to claim 1 wherein the decarbonylation is carried out at a temperature of 20° to 250° C.

23. A process according to claim 22 wherein decarbonylation is performed at a temperature of 30° to 220° C.

24. A process according to claim 1 wherein the formiate is decarbonylated in a heterogeneous reaction mixture in the absence of a solvent.

25. A process according to claim 1 wherein the formiate is decarbonylated in the presence of an inert reaction medium and in the presence of a solvent.

26. A process according to claim 1, wherein the decarbonylation is carried out in the melt and carbon monoxide is withdrawn from the reaction mixture.

27. A process according to claim 1, wherein the decarbonylation is carried out in the presence of a tertiary alcohol and carbon monoxide is withdrawn from the reaction mixture.

28. A process according to claim 1, wherein the decarbonylation is carried out at a temperature of 20° to 250° C.

29. A process according to claim 28, wherein the decarbonylation is carried out at a temperature of 30° to 220° C.

30. A process according to claim 1, wherein said solvent is p-xylylene glycol.

31. A process according to claim 1, wherein said solvent is m-xylylene glycol.

32. A process according to claim 1, wherein the process is carried out in the presence of an alcohol corresponding to the formic acid ester reactant.

* * * * *